United States Patent
Davis et al.

(10) Patent No.: US 10,117,605 B2
(45) Date of Patent: Nov. 6, 2018

(54) SYSTEM, METHOD AND APPARATUS FOR PATIENT COMMUNICATIONS IN REMOTE HEARING DIAGNOSTICS

(71) Applicants: Dave Davis, Spring Mount, PA (US); Brian Lisiewski, Millsboro, DE (US)

(72) Inventors: Dave Davis, Spring Mount, PA (US); Brian Lisiewski, Millsboro, DE (US)

(*) Notice: Subject to any disclaimer, the term of this patent is extended or adjusted under 35 U.S.C. 154(b) by 0 days.

(21) Appl. No.: 15/296,136

(22) Filed: Oct. 18, 2016

(65) Prior Publication Data
US 2018/0103876 A1    Apr. 19, 2018

(51) Int. Cl.
*A61B 7/04*     (2006.01)
*A61B 5/12*     (2006.01)
*A61B 5/00*     (2006.01)
*H04R 25/00*    (2006.01)
*H04L 29/08*    (2006.01)

(52) U.S. Cl.
CPC .......... *A61B 5/123* (2013.01); *A61B 5/0022* (2013.01); *A61B 5/7465* (2013.01); *H04R 25/70* (2013.01); *H04L 67/12* (2013.01); *H04L 67/141* (2013.01); *H04R 2225/55* (2013.01); *H04R 2420/03* (2013.01); *H04R 2430/01* (2013.01)

(58) Field of Classification Search
CPC ..... A61B 5/123; A61B 5/0022; A61B 5/7465; H04R 29/001
See application file for complete search history.

(56) References Cited

U.S. PATENT DOCUMENTS

| | | | | |
|---|---|---|---|---|
| 2009/0062687 | A1* | 3/2009 | Givens | A61B 5/121 600/559 |
| 2010/0109749 | A1* | 5/2010 | Chen | G06F 13/385 327/419 |
| 2010/0310101 | A1* | 12/2010 | Anderson | A61B 5/11 381/309 |
| 2011/0261972 | A1* | 10/2011 | Komm | H04H 60/04 381/74 |
| 2013/0343583 | A1* | 12/2013 | Marcoux | H04R 25/70 381/314 |
| 2014/0186807 | A1* | 7/2014 | Rastatter | G09B 5/06 434/169 |
| 2016/0100243 | A1* | 4/2016 | Wismar | H04R 1/1041 381/74 |
| 2017/0180923 | A1* | 6/2017 | Barron | H04W 4/02 |

* cited by examiner

*Primary Examiner* — Simon King

(57) ABSTRACT

Method, system and apparatus for patient communications in remote hearing diagnostics is disclosed. The invention may include electrical circuitry for conditioning audio input and output signals as well as a means of switching paths for the audio data between equipment sources and personnel involved in a remote hearing diagnostics session.

15 Claims, 2 Drawing Sheets

SYSTEM, METHOD AND APPARATUS FOR PATIENT COMMUNICATIONS IN REMOTE HEARING DIAGNOSTICS

FIELD OF THE INVENTION

The present invention relates to the field of hearing diagnostics, and particularly in the area of tele-audiology, or the remote operation and administration of a diagnostic hearing test procedure.

BACKGROUND OF THE INVENTION

In audiology, communicating with a patient who is not within range of normal voice communication is performed in a variety of ways, depending on the type of diagnostic test being performed and office setting. In hearing diagnostics, a patient is often isolated in a sound-treated enclosure or booth to ensure that ambient noise does not affect the testing process and results. In some countries outside the United States, the hearing care provider and patient sit together in a sound-treated room. Whenever a hearing care specialist is not face to face with the patient, a patient communications subsystem must be present to facilitate the interchange between the hearing care provider and the patient. This is necessary so that the patient and the hearing care provider can communicate verbally to provide instructions and feedback, and to ensure the safety and comfort of the test subject and also the accuracy of the test result. In audiometry in particular, above and beyond basic verbal communication, speech testing is routinely conducted and often requires that the patient repeat a word or phrase that the tester can hear and score as part of a comprehensive evaluation of a patient's hearing and/or cognitive ability.

In systems designed for audiometry, a built-in port for a microphone and for speaker(s) is implemented to make this possible, and patch cords or other means can be used to connect across physical boundaries such as the enclosure of a sound-proof booth. This configuration is routinely implemented in various countries and regions including the United States, and offers acceptable audio quality for the communication between the hearing care provider and the patient being evaluated.

BRIEF SUMMARY OF THE INVENTION

In order to provide a facility to enable patient communication when the hearing care professional is located at a distance from the patient, whether down the hall or across the globe, an alternate and more complex configuration is required. For instance, if an audiologist wishes to remotely observe, administer or control a diagnostic test of a patient at a different location such as another office or the patient's home, the configuration must accommodate the ability to connect and the audio streams traverse a medium such as a local or wide-area network or across the Internet. This introduces the need to bridge the distance using a method and apparatus to ensure that the audio channels are enabled and the quality of the audio is suitable to achieve the communication at a level similar to the quality if the patient and hearing care professional are face to face.

The purpose of such a system and apparatus are several fold, including the ability to extend the communications across a distance, as well as to enable multiple participants in the process to verbally communicate. In certain instances and settings, such as when two distant locations are bridged together to effect a remote diagnostics session, it is often desirable that at least one additional person be involved and located at the patient location, in order to provide assistance to the patient in determining both adequacy of the test conditions and also to ensure that any transducers or probes used for the diagnostic process are correctly placed or operated with respect to the test subject. In this situation, it is common to expect that the remote hearing care professional may have a need or desire to communicate with both the assistant/technician as well as the patient. This situation would indicate the need for one or more mechanisms to be implemented as an additional part of the patient communications system, and allow for any of several communications paths to be enabled or disabled depending on the clinical situation at hand.

Further, the invention must provide the flexibility to reversibly adapt to the setting and communications method used, and therefore offer the ability to be easily inserted and reversibly removed from use in the configuration of the hearing diagnostics process.

In at least one embodiment, to enable the communication between a hearing care professional and patient when at a distance, a computing device connected to each end facilitates the remote access. However, given that audio ports on a computer are typically designed to use with directly connected peripherals (such as headset comprised of headphones and microphone) and that the ports on hearing diagnostic devices are not compatible with this, a special type of apparatus is required. Further, since it is often desirable to have a trained assistant co-located with the patient at the site, and that the assistant may also need to communicate with the remote hearing care provider, the apparatus in question should also allow for this option.

Thus, a system, method and apparatus is needed to help resolve the issues depicted above, and provide a flexible and electrically suitable solution to the variety of configurations and connections that are required to effectuate proper and high-quality communication between all parties across a distance.

The present invention addresses the needs identified and provides a solution that is implemented in digital circuitry and port configurations with appropriate switching that can be housed in a small form factor for convenience and portability. Alternatively, the system and apparatus can be implemented as part of a medical device circuitry, but in the preferred embodiment and in most instances the solution will be configured as an adapter that can be added and removed as required to reversibly adapt diagnostic equipment for use in remote diagnostic testing. Further, the use of commonly available cables with various types of plugs can be used to ensure that flexibility is maintained in how to adapt the inventive device to connect with and operate in conjunction with various types of diagnostic equipment and computing device ports. For instance, while many diagnostic devices (such as audiometers) may use ⅛" (3.5 mm.) plugs for microphone and speaker/headphone outputs, some may use other plugs such as ¼" audio jacks, mini-DIN, or other such connectors. The use of off-the-shelf or custom built cables to enable the connection to and from the inventive device offers the maximum flexibility in configuring and adapting the audio connections between a computing device and the diagnostic equipment ports.

BRIEF DESCRIPTION OF THE DRAWINGS

Features of the present invention are further apparent from the following detailed description of the embodiments of the present invention taken in conjunction with the accompanying drawings, of which.

DETAILED DESCRIPTION OF THE INVENTION

In a preferred embodiment, the invention provides electronics and a switching mechanism in a portable enclosure that may include a variety of input and output connectors. The device housing (100) as shown in FIG. 1 may include an electronic assembly within the unit that provides the circuitry and components that enable both the conditioning of the input and output electrical feeds as well as the switching mechanism that properly directs the path of the audio signals.

Figure 1:
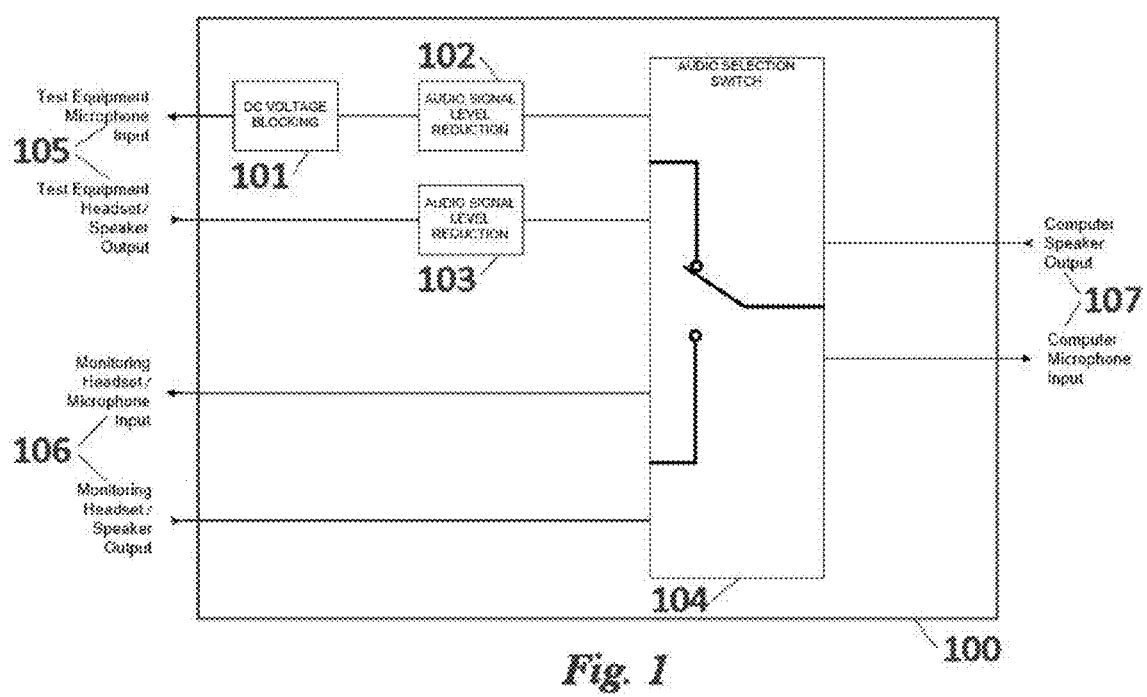
FIG. 1 depicts a block diagram of the functional operation of the inventive device.

FIG. 1 shows an example embodiment of the invention (100) with input and output connectors for cables to connect the speaker and microphone of the diagnostic test equipment (105), the monitor speaker/microphone headset for the local assistant (106), and the computer speaker and microphone (107). These pairs of connectors may be labeled to facilitate proper connecting with the input/output from the designated devices. Within the portable enclosure (100), the mechanisms to ensure proper electrical pathway and conditioning are present. The DC (Direct Current) voltage blocking (101) function is implemented due to the fact that computer microphone input circuits provide a DC bias required to power active microphones. This biasing voltage needs to be eliminated prior to the analog to digital conversion process, and the circuitry required to perform this function is included in the device.

The function of the audio signal reduction for both speaker and microphone originating from the diagnostic equipment (102 and 103), are included as the powered output levels for speakers need to be reduced to standard audio line level prior to the analog to the digital conversion process. The audio selection switch (104) enables the pathway from either the diagnostic equipment to the computer ports and on to the remote operator's speaker and microphone, or from the monitoring assistant's speaker and microphone headset to the computer and on to the remote operator's speaker and microphone. The switch can also be implemented as a three-way option that would add the possibility of the assistant being able to hear and optionally interact verbally with the patient and the remote hearing care provider during the testing process.

The above configuration may be varied in order to accommodate a range of potential housing shapes and preferred operational formats without affecting the principal function of the device (100).

Figure 2:
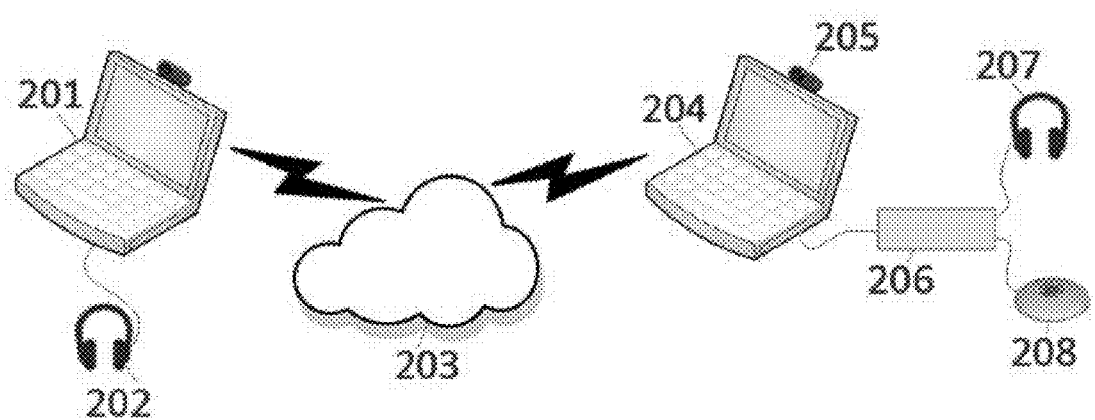
FIG. 2 illustrates the configuration of the device as part of the patient communications system that facilitates the remote audio connections and routing for the preferred embodiment of the invention.

FIG. 2 shows an illustrative configuration of the system that includes the inventive device as a means to condition and route the audio communications to the intended path.

A computer (or tablet, smartphone or other such computing device) (201) is equipped with a headset with microphone and speaker (202) or optionally a separate speaker and microphone for use in connecting to another computing device (204) via a computer network such as the Internet (203). The computer (or tablet, smartphone or other such computing device) (204), also connected to a computer network such as the Internet (203) may optionally have a webcam or other type of videoconferencing camera (205) to enable an audio/video session with the remote computer (201). The inventive device (206) is connected to the computer's (205) speaker and microphone ports, and also to both the assistant's headset (comprised of a speaker and microphone) (207) and also the speaker and microphone ports of the diagnostic test equipment (208).

By connecting the inventive device in the above described configuration, the remote operator of the computing device (201) may operably interface with the diagnostic test equipment (208) and interact with the patient during a test session using the diagnostic test equipment via audio communications and optionally video communications if the camera (205) is available on both the remote (201) and local (205) computer. In an alternate path which can be selected via the switch mechanism of the inventive device, the audio communications path my be redirected to the assistant's headset (207). In this alternate path selection, the remote operator may talk with the local assistant via the audio connection provided by the inventive device, and thereby provide instructions and/or interact with the assistant to discuss the test process, results, or share other relevant information about the diagnostic testing process.

Thus, a portable addition to a patient communications subsystem of diagnostic test equipment has been described that provides the needed electrical and mechanical features to accomplish both the conditioning and routing of the audio communications channel, thereby enhancing both the utility and the flexibility of the system in which the device is inserted. Those skilled in the art will appreciate that numerous changes and modifications can be made to the preferred embodiment of the invention, and that such changes and modifications can be made without departing from the spirit of the invention.

The invention claimed is:

1. Apparatus for patient communications in remote hearing diagnostics between a computer having a computer microphone input and a computer speaker output, a hearing diagnostics test equipment having a test equipment microphone input and a test equipment speaker output, and a second microphone input and speaker output, the apparatus comprising:

a direct current (DC) voltage blocking circuit that eliminates a biasing voltage sourced by the test equipment microphone input;

a first audio signal level reduction circuit for reducing a signal level of an audio signal provided to the test equipment microphone input;

a second audio signal level reduction circuit for reducing a signal level of an audio signal received from the test equipment speaker output; and an audio selection switch that enables a selectable electrical connection from the computer to either the test equipment microphone input and speaker output or to the second microphone input and speaker output.

2. The apparatus of claim 1, wherein each of the audio signal level reduction circuits reduces powered output levels provided by the speakers outputs.

3. The apparatus of claim 1, further comprising at least one connector for connecting the test equipment microphone input and speaker output to the apparatus.

4. The apparatus of claim 1, further comprising at least one connector for connecting the computer microphone input and speaker output to the apparatus.

5. The apparatus of claim 1, further comprising at least one connector for connecting the second microphone input and speaker output to the apparatus.

6. A system for patient communications in remote hearing diagnostics, the system comprising:
- a first computing device having a computer microphone input and a computer speaker output;
- a first headset having a first headset microphone input and a first headset speaker output;
- diagnostic test equipment having a test equipment microphone input and a test equipment speaker output; and
- an adapter that is connected to the first computing device, the first headset, and the diagnostic test equipment, wherein the adapter comprises:
  - a direct current (DC) voltage blocking circuit that eliminates a biasing voltage sourced by the test equipment microphone input;
  - a first audio signal level reduction circuit for reducing a signal level of an audio signal provided to the test equipment microphone input;
  - a second audio signal level reduction circuit for reducing a signal level of an audio signal received from the test equipment speaker output; and
  - an audio-selection switch that enables a selectable electrical connection from the first computing device to either the diagnostic test equipment microphone input and speaker output or to the first headset microphone input and speaker output.

7. The system of claim 6, wherein the adapter is removably coupled to the diagnostic test equipment.

8. The system of claim 7, wherein the adapter is removably coupled to the first headset.

9. The system of claim 8, wherein the adapter is removably coupled to the first computing device.

10. The system of claim 6, further comprising a second computing device that is connected to the first computing device via a computer network.

11. The system of claim 10, wherein the second computing device is equipped with a second headset, the second headset having a second headset microphone input and a second headset speaker output.

12. The system of claim 10, wherein the computer network is the Internet.

13. The system of claim 10, wherein the first computing device includes a webcam or other type of conferencing device that enables audio/video sessions with the second computing device.

14. The system of claim 6, wherein the first computing device is one of a desktop, laptop, tablet, or smartphone.

15. The system of claim 6, wherein the adapter is removably coupled to the computer speaker output and computer microphone input of the first computing device.

* * * * *